(12) United States Patent
Yamada

(10) Patent No.: US 8,241,291 B2
(45) Date of Patent: *Aug. 14, 2012

(54) SINUS MEMBRANE LIFTING AND LATERAL SEPARATION INSTRUMENT

(76) Inventor: Jason M. Yamada, Rolling Hills Estates, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/931,082

(22) Filed: Jan. 24, 2011

(65) Prior Publication Data

US 2011/0117519 A1 May 19, 2011

Related U.S. Application Data

(63) Continuation of application No. 11/895,811, filed on Aug. 28, 2007, now abandoned.

(60) Provisional application No. 60/882,940, filed on Dec. 31, 2006.

(51) Int. Cl.
*A61F 2/46* (2006.01)

(52) U.S. Cl. ...................... 606/86 R; 433/141

(58) Field of Classification Search .......... 433/141–148, 433/72, 42, 45, 165; 606/80, 190, 86 R; 600/208, 237–242; D24/133, 146, 154

See application file for complete search history.

(56) References Cited

U.S. PATENT DOCUMENTS

| | | | | | |
|---|---|---|---|---|---|
| 1,245,153 | A | * | 11/1917 | Evslin | 433/136 |
| 4,259,069 | A | * | 3/1981 | Lustig | 433/144 |
| 4,579,116 | A | * | 4/1986 | Catalano | 606/107 |
| 5,030,091 | A | * | 7/1991 | Svanberg | 433/143 |
| 5,676,544 | A | * | 10/1997 | Urban | 433/147 |
| 6,022,217 | A | * | 2/2000 | Hugo | 433/166 |
| 6,206,698 | B1 | * | 3/2001 | Billingsley | 433/164 |
| 6,733,496 | B2 | * | 5/2004 | Sharkey et al. | 606/41 |
| D522,141 | S | * | 5/2006 | Chung | D24/152 |
| 7,249,948 | B2 | * | 7/2007 | Hill | 433/143 |
| 7,662,188 | B2 | * | 2/2010 | Yamada | 623/17.17 |
| 2007/0275348 | A1 | * | 11/2007 | Lemon | 433/119 |

* cited by examiner

*Primary Examiner* — Cris L Rodriguez
*Assistant Examiner* — Edward Moran
(74) *Attorney, Agent, or Firm* — Robert R. Meads

(57) ABSTRACT

A sinus membrane lifting instrument comprising a longitudinally extending handle portion, an angled neck extending longitudinally from the handle portion and a disc-shaped tip extending from the angled neck, the angled neck including means for sensing tension in a sinus membrane as it is being lifted by the instrument from its bony support floor.

5 Claims, 2 Drawing Sheets

SINUS MEMBRANE LIFTING AND LATERAL SEPARATION INSTRUMENT

RELATED PATENT APPLICATIONS

The present application is a continuation of U.S. patent application Ser. No. 11/895,811, filed Aug. 28, 2007, now abandoned and claims the benefit of U.S. Provisional Patent application Ser. No. 60/882,940, filed Dec. 31, 2006, which is incorporated herein by reference. The present application also relates to the subject matter of the U.S. patent application Ser. No. 11/895,823, filed Aug. 28, 2007, entitled "Internal Sinus Manipulation (ISM) Procedure For Facilitating Sinus Floor Augmentation In Dental Procedures", now U.S. Pat. No. 7,662,188 issued Feb. 16, 2010, which is also incorporated herein by this reference.

BACKGROUND OF INVENTION

As stated in the above-identified U.S. Pat. No. 7,662,188, during the described procedure and following the formation of an upward channel in the bone leading to the sinus floor of a patient, there is a simultaneous and controlled lifting and lateral separation of an exposed portion of the sinus membrane from the sinus floor to form an open pocket between the sinus floor and the sinus membrane. Such sinus pocket formation is accomplished using a sinus lifting tool or instrument. The present invention is directed to a preferred form of that instrument.

SUMMARY OF INVENTION

Basically, the sinus lifting instrument of the present invention comprises a disk-shaped tip and an angled neck extending longitudinally from a handle portion of the instrument. The disk-shaped tip is designed to release the sinus membrane from the bony wall of sinus floor. The angled neck is designed to aid in the proper positioning of the working tip. An inflection portion of the angled neck extending from the working tip allows a clinician to feel the tension of the sinus membrane and to determine the amount of initial lateral and vertical membrane reflection.

As illustrated in FIG. 3 of the U.S. Pat. No. 7,662,188 by solid, dashed and broken line outlines of the instrument, in the formation of the sinus pocket, the instrument is simultaneously raised and turned back and forth on a vertically extending axis with the tip simultaneously lifting and laterally separating the membrane from the sinus floor to form and enlarge the pocket. This procedure of simultaneous membrane lateral release and elevation is continued until a planned amount of sinus extension is achieved and the small open pocket is defined.

BRIEF DESCRIPTION OF ACCOMPANYING DRAWINGS

DETAILED DESCRIPTION OF INVENTION

Figure 1:
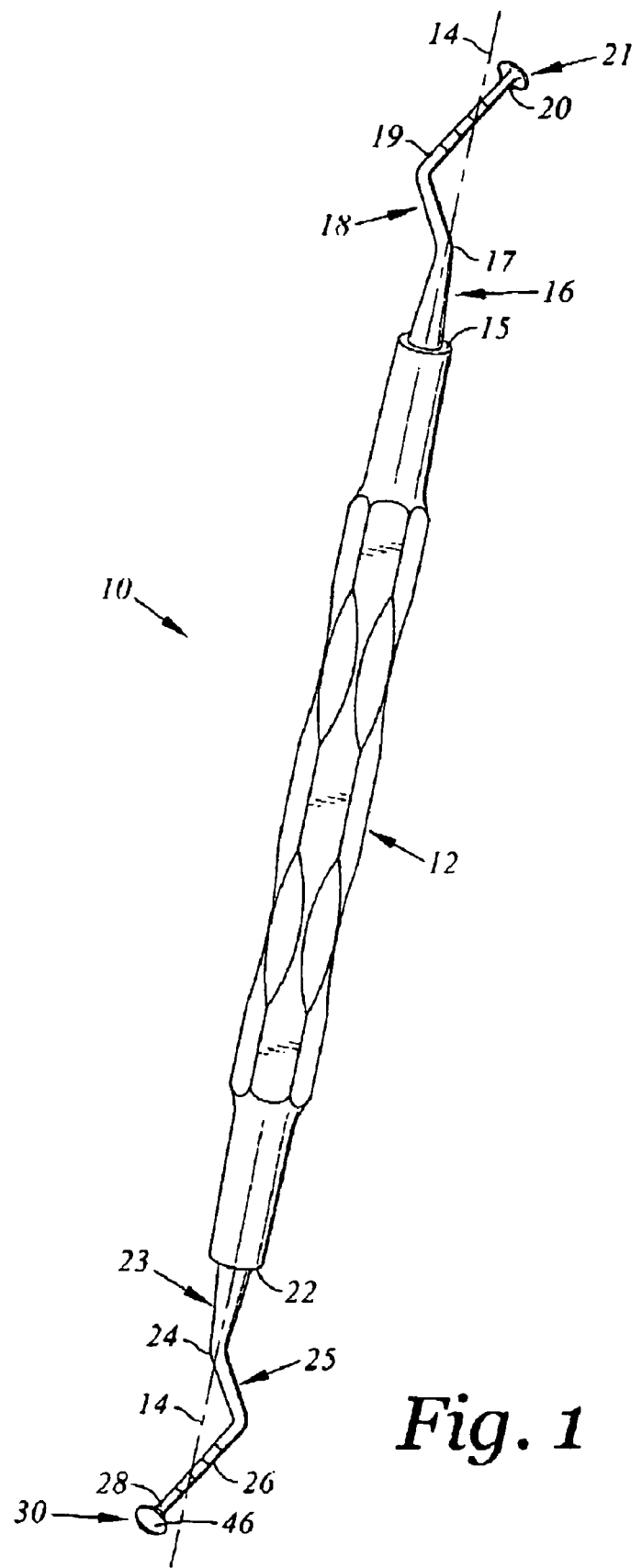
FIG. 1 is a perspective view of the preferred sinus lifting instrument including a central axially elongated handle portion having angled necks and disc-shaped tips extending from opposite ends of the handle portion.

As depicted in FIG. 1, the sinus lifting instrument 10 of the present invention comprises an elongated central handle portion 12 extending longitudinally on a longitudinal axis 14 of the instrument. Connected to and extending longitudinally from an upper end 15 of the central handle portion 12 is an upper frusto-conical connecting portion 16 extending longitudinally on the axis 14 and supporting at its upper end 17 an upper angled neck 18 including an inflection portion 19. An upper end 20 of the inflection portion 19 supports an upper disc-shaped tip 21. Connected to and extending longitudinally from a lower end 22 of the central handle portion 12 is a lower frusto-conical connecting portion 23 extending longitudinally on the axis 14 and supporting at its lower end 24 a lower angled neck 25 including an inflection portion 26. A lower end 28 of the inflection portion 26 supports a lower disc-shaped tip 30.

Figure 2:
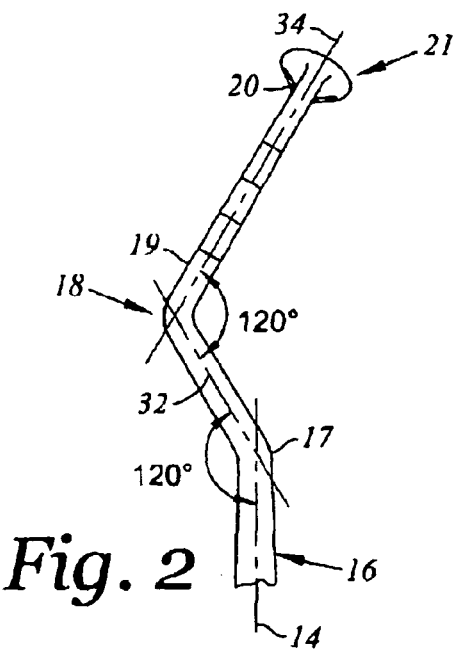
FIG. 2 is an enlarged fragmentary front view of the upper end portion of the instrument as illustrated in FIG. 1 showing the upper angled neck and disc-shaped tip thereof.

As illustrated in FIG. 2, the upper connecting portion 16 extends upward longitudinally along the instrument axis 14 and at its upper end 17 connects to and supports the angled neck 18. From its connection to the portion 16, the angled neck 18 extends upwardly along an axis 32 that forms an obtuse angle with the axis 14. As depicted in FIG. 2, the axis 32 preferably forms an obtuse angle of about 120 degrees with the axis 14. As also shown in FIG. 2, the inflection portion 19 of the angled neck 18 also extends longitudinally upwardly along an axis 34 that forms an obtuse angle of preferably about 120 degrees with the axis 32. Thus constructed, the upper end 20 of the inflection portion 19 supports the disc-shaped tip 21.

Figure 4:
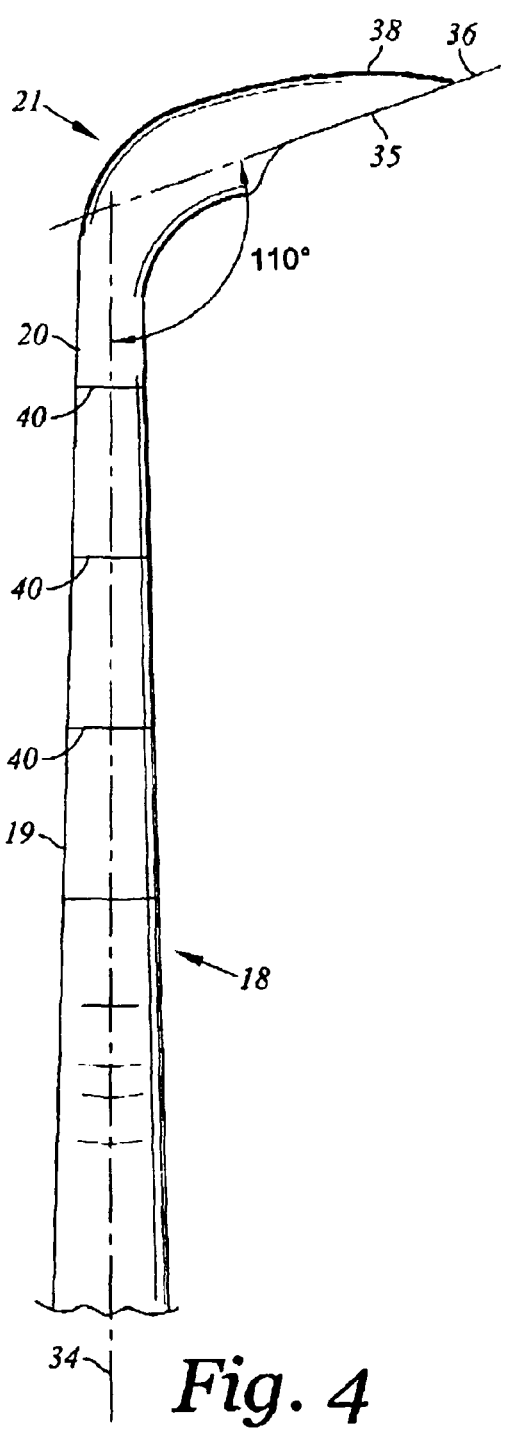
FIG. 4 is a further enlarged fragmentary side view of the upper disc-shaped tip portion shown in FIG. 2.

As illustrated most clearly in FIG. 4, a lower surface 35 of the disc-shaped tip 21 extends rearward from the inflection portion 19 along an axis 36 that forms an obtuse angle of preferably about 110 degrees with the axis 34 of the inflection portion. As depicted in FIGS. 1 and 2, the lower surface 35 of the disc-shaped tip 21 is flat and substantially circular in the plane of the lower surface while an upper surface 38 of the tip 21 is upwardly curved, having a smooth substantially concave shape (when viewed from the bottom) and a diameter of about 1.8 millimeters.

Also, as illustrated most clearly in FIG. 4, the inflection portion 19 of the angled neck 18 carries a series of evenly spaced marks 40 for indicating to the instrument user the distance that the instrument 10 has penetrated a sinus pocket in lifting and laterally separating the sinus membrane from the sinus floor during formation of the sinus pocket using the instrument 10. In that regard, as the upper end of the instrument 10 shown in FIG. 1 penetrates an upper end of the bone channel leading to the sinus membrane, the curved upper surface 38 of the disc-shaped tip 21 engages and in combination with the angled neck 18 and its inflection portion 19 gently lifts the sinus membrane from the sinus floor of the patient. With lateral movement of the instrument 10 within the sinus pocket, the disc-shaped tip gently lifts more of the sinus membrane from the sinus floor to laterally enlarge the sinus pocket. With further upward movement of the instrument 10 within the sinus pocket, the curved upper surface 38 of the disc-shaped tip 21 further lifts the sinus membrane to enlarge the sinus pocket to its desired size and shape.

Figure 3:
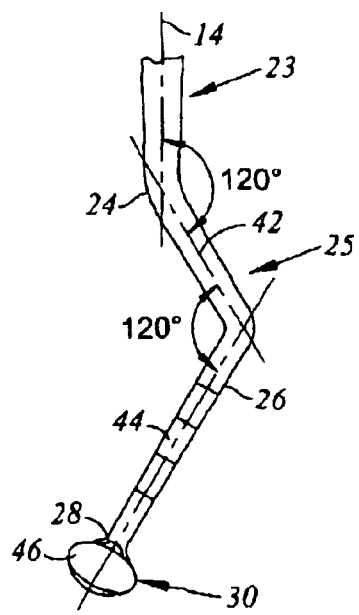
FIG. 3 is an enlarged fragmentary front view of the lower end portion of the instrument as illustrated in FIG. 1 showing the lower angled neck and disc-shaped tip thereof.

When the instrument 10 shown in FIG. 1 is inverted, the curved surface of the lower disc-shaped tip 30 in combination with the angled neck 25 and its inflection portion 26 provide the same functional features in gently lifting and laterally separating the sinus membrane from the sinus floor to form and enlarge a sinus pocket to a desired size and shape. In that regard, and with specific reference to FIG. 3, the shape and dimensions of the lower portion of the instrument 10 shown in FIG. 3 follow those shown and described relative to FIG. 2. Specifically, the lower connecting portion 23 extends downward and longitudinally along the instrument axis 14 and at its lower end 24 connects to and supports the angled neck 25. From its connection to the portion 23, the angled neck 25 extends downwardly long an axis 42 that forms an obtuse angle with the axis 14. As depicted in FIG. 3, the axis 42 preferably forms an obtuse angle of about 120 degrees with the axis 14. As also shown in FIG. 3, the inflection portion 26 of the angled neck 25 also extends longitudinally downward along an axis 44 that forms an obtuse angle of preferably about 120 degrees with the axis 42. Thus constructed, the lower end 28 of the inflection portion 26 supports the disc-shaped tip 30.

As illustrated most clearly in FIG. 4 and as described with respect to the upper portion of the instrument 10, when the instrument is inverted a lower surface of the disc-shaped tip 30 will extend rearward from the inflection portion 26 along an axis that forms an obtuse angle of preferably about 110 degrees with the axis 44 of the inflection portion 26. As depicted in FIGS. 1 and 3, a lower surface 46 of the disc-shaped tip 30 is flat and substantially circular in the plane of the lower surface while an upper surface of the tip 30 is upwardly curved, having a smooth substantially concave shape (when viewed from the bottom) and a diameter of about 1.8 millimeters.

While a particular preferred embodiment of the sinus membrane lifting instrument has been illustrated and described above, it is appreciated that changes and modifications may be made in the illustrated embodiment without departing from the spirit of the invention. Accordingly, the scope of present invention is to be limited only by the terms of the following claims.

The invention claimed is:

1. A sinus membrane lifting instrument, the instrument comprising:
   an elongated handle portion extending longitudinally along a longitudinal axis of the instrument;
   an angled neck extending longitudinally at an upward angle outward from the handle portion toward a tip along an axis that forms an obtuse angle with the longitudinal axis of the instrument;
   an inflection portion extending upward within an upper end of the angled neck supporting the tip along an axis that forms an obtuse angle with the axis of the angled neck;
   the tip being disc-shaped and supported on and by and extending at an upward angle from an upper end of the inflection portion of the angled neck and having (i) a smooth upwardly curved upper surface for positioning by the angled neck against an exposed portion of the sinus membrane and (ii) a flat lower surface extending rearward from and opposite the direction of the inflection portion along an axis that forms an obtuse angle with the axis of the inflection portion;
   the inflection portion in combination with the angled neck and tip comprising sinus membrane tension sensing means for a user of the instrument; and the instrument being capable of (i) gently lifting a portion of a sinus membrane from the bony floor of a patient's sinus to form a small open pocket in the sinus membrane between the bony floor and the sinus membrane and (ii) then laterally moving over the bony floor and turning and further lifting the sinus membrane within the open pocket to render the pocket ready to receive bone grafting material which when cured will form additional bone for supporting a dental implant, all without causing damage to the sinus membrane.

2. The sinus membrane lifting instrument of claim 1 wherein the axis of the angled neck forms an obtuse angle of about 120 degrees with the longitudinal axis of the lifting instrument.

3. The sinus membrane lifting instrument of claim 2 wherein the obtuse angle of the axis of the inflection portion relative to the axis of the angled neck is about 120 degrees.

4. The instrument of claim 3 wherein the obtuse angle between the axis of the flat lower surface of the disc-shaped tip and the axis of the inflection portion is about 110 degrees.

5. The instrument of claim 4 wherein the lower surface of the disc-shaped tip is flat and substantially circular in the plane of the lower surface.

* * * * *